US011246647B2

(12) United States Patent
Schostek et al.

(10) Patent No.: US 11,246,647 B2
(45) Date of Patent: Feb. 15, 2022

(54) MEDICAL DC CURRENT GENERATOR AND BIPOLAR MEDICAL IMPLANT FRAGMENTATION DEVICE EQUIPPED THEREWITH

(71) Applicant: OVESCO ENDOSCOPY AG, Tuebingen (DE)

(72) Inventors: Sebastian Schostek, Tuebingen (DE); Chi-Nghia Ho, Reutlingen (DE); Thomas Gottwald, Kochel am See (DE); Marc Schurr, Tuebingen (DE)

(73) Assignee: Ovesco Endoscopy AG

( * ) Notice: Subject to any disclaimer, the term of this patent is extended or adjusted under 35 U.S.C. 154(b) by 626 days.

(21) Appl. No.: 15/592,036

(22) Filed: May 10, 2017

(65) Prior Publication Data

US 2018/0000538 A1    Jan. 4, 2018

(30) Foreign Application Priority Data

May 11, 2016  (EP) ..................................... 16169234

(51) Int. Cl.
*A61B 18/14* (2006.01)
*A61B 18/00* (2006.01)
(Continued)

(52) U.S. Cl.
CPC ...... *A61B 18/1447* (2013.01); *A61B 18/1206* (2013.01); *A61B 18/1445* (2013.01);
(Continued)

(58) Field of Classification Search
CPC ............ A61B 18/1206; A61B 18/1445; A61B 18/1447; A61B 2018/00601;
(Continued)

(56) References Cited

U.S. PATENT DOCUMENTS 7,742,795 B2   6/2010  Stone et al.
10,881,454 B2  1/2021  Schostek et al.
(Continued)

FOREIGN PATENT DOCUMENTS

CN   102125430 A   7/2011
EP     2967712 A1  1/2016
(Continued)

OTHER PUBLICATIONS

European Search Report, dated Feb. 12, 2016, European application No. 16169234.8.
(Continued)

*Primary Examiner* — Tigist S Demie
(74) *Attorney, Agent, or Firm* — RatnerPrestia

(57) ABSTRACT

The present invention is directed to an endoscopic implant cutting and/or fragmenting apparatus of the bipolar type, operating on direct current, comprising an endoscope instrument having at least two opposing electrodes at its distal instrument head forming a cutting gap inbetween for receiving an electrically conductive implant or implant section to generate punctiform physical contact with the implant, and a DC-impulse generator connected to a control device adapted to generate a direct current in a pulsed way such that in a first phase of physical contact, the current pulse is adjusted to induce electric energy into the implant material being sufficient to melt the implant material exclusively in the area of the contact portion and in a second phase of physical noncontact, the current pulse is adjusted to generate an electric arc between at least one electrode and the melted implant material being sufficient to cut the melted implant material.

19 Claims, 9 Drawing Sheets

(51) Int. Cl.
*A61B 18/12* (2006.01)
*A61F 2/82* (2013.01)

(52) U.S. Cl.
CPC ............ *A61B 2018/0072* (2013.01); *A61B 2018/00601* (2013.01); *A61B 2018/00702* (2013.01); *A61B 2018/00714* (2013.01); *A61B 2018/00761* (2013.01); *A61B 2018/00767* (2013.01); *A61B 2018/00875* (2013.01); *A61B 2018/126* (2013.01); *A61B 2018/1213* (2013.01); *A61B 2018/1266* (2013.01); *A61B 2018/142* (2013.01); *A61B 2018/1452* (2013.01); *A61F 2/82* (2013.01); *A61F 2240/001* (2013.01)

(58) Field of Classification Search
CPC .......... A61B 2018/00702; A61B 2018/00714; A61B 2018/0072; A61B 2018/00761; A61B 2018/00767; A61B 2018/00875; A61B 2018/1213; A61B 2018/126; A61B 2018/1266; A61B 2018/142; A61B 2018/1452; A61F 2240/001; A61F 2/82
See application file for complete search history.

(56) References Cited

U.S. PATENT DOCUMENTS

| | | |
|---|---|---|
| 2009/0204064 A1 | 8/2009 | Farin et al. |
| 2010/0087834 A1 | 4/2010 | Eisele et al. |
| 2016/0022356 A1* | 1/2016 | Schostek ............ A61B 18/1445 606/48 |

FOREIGN PATENT DOCUMENTS

| | | |
|---|---|---|
| JP | 2016509908 A | 4/2016 |
| WO | 2013096584 A2 | 6/2013 |
| WO | 2014140039 | 9/2014 |

OTHER PUBLICATIONS

Notification of Reasons for Rejection for Japanese Application No. 2017-094312, dated Feb. 10, 2021, 8 pages.
Chinese Office Action for Chinese Application No. 201710329911.2, dated Nov. 4, 2020 with translation 20 pages.

* cited by examiner

| Material | Specific electrical resistance Ω·m | Linear temperature coefficient 1/K | Melting point | Specific heat capacity in kJ/(kg·K) | Specific density in kg/m³ | Specific thermal conductivity in W/(m·K) | Thermal diffusivity in mm²/s |
|---|---|---|---|---|---|---|---|
| Silver | 1,59·10⁻⁸ | 0,0039 | 961 | 0,235 | 10497 | 2,28 | 143 |
| Copper | 1,68·10⁻⁸ | 0,0039 | 1064 | 0,382 | 8960 | 3,51 | 210 |
| Gold | 2,44·10⁻⁸ | 0,0034 | 1084 | 0,130 | 19290 | 2,62 | 107 |
| Tungsten | 5,6·10⁻⁸ | 0,0045 | 3422 | 0,134 | 19800 | 8,62 | 154 |
| Iron | 1,0·10⁻⁷ | 0,005 | 1536 | 0,452 | 7500 | 5,08 | 50,8 |
| Steel unalloyed | 1,43·10⁻⁷ | 0,0057 | 1493 | 0,490 | 7800 | 5,56 | 39,0 |
| Titanium | 4,2·10⁻⁷ | 0,0038 | 1668 | 0,522 | 4505 | 3,83 | 9,12 |
| Stainless steel | 6,9·10⁻⁷ | 0,0009 | 1147 | 0,477 | 7800 | 4,13 | 5,99 |
| Nickel-Titanium (Martensit) | 7,6·10⁻⁷ | 0,0018 | 1310 | 0,45 | 6450 | 3,69 | 4,86 |
| Muscle tissue | 2 | | | | | | |
| Drinking water | 20 bis 2000 | | | 4,182 | | | |
| Distilled water | 180000 | | | | | | |

Fig. 3

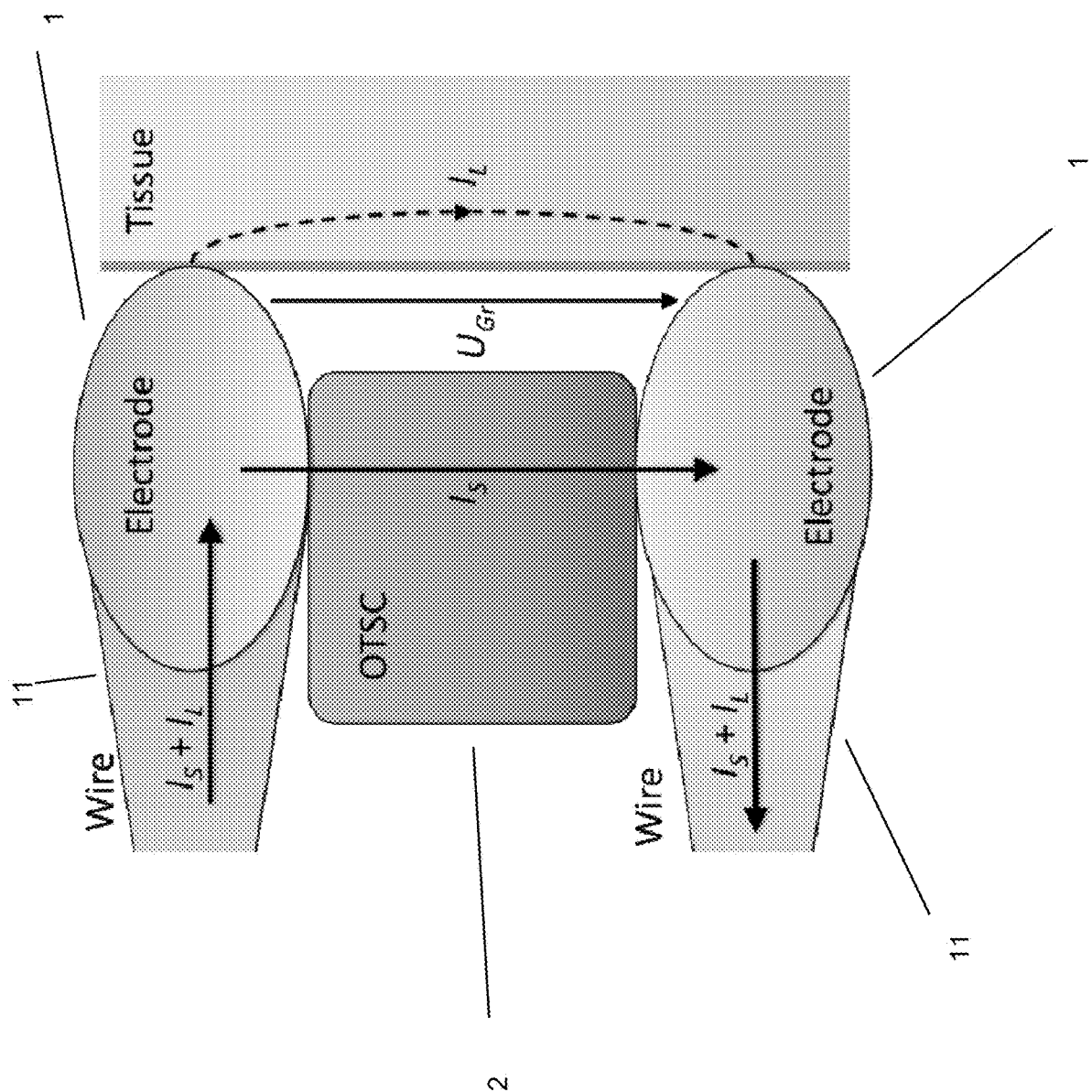

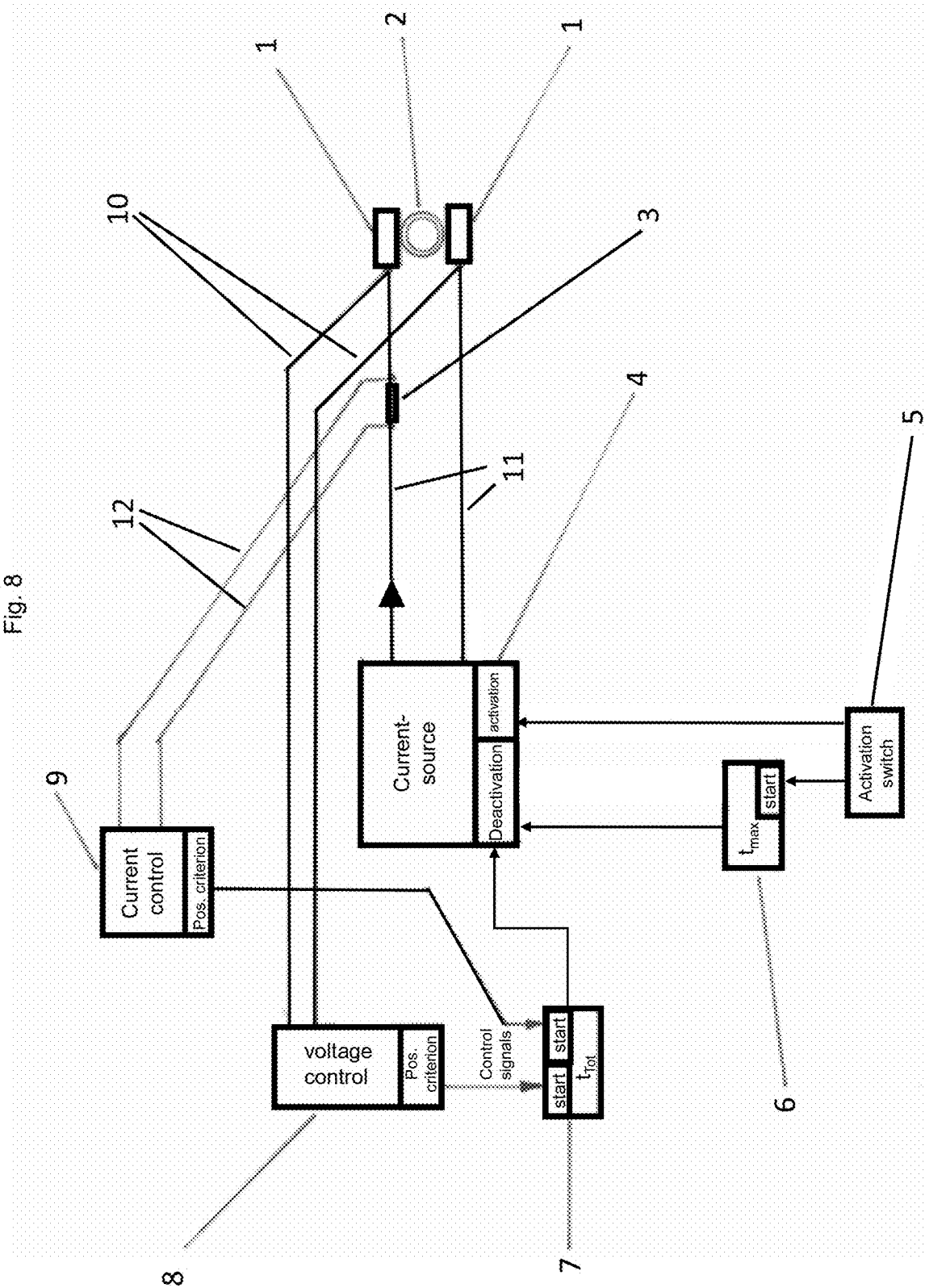

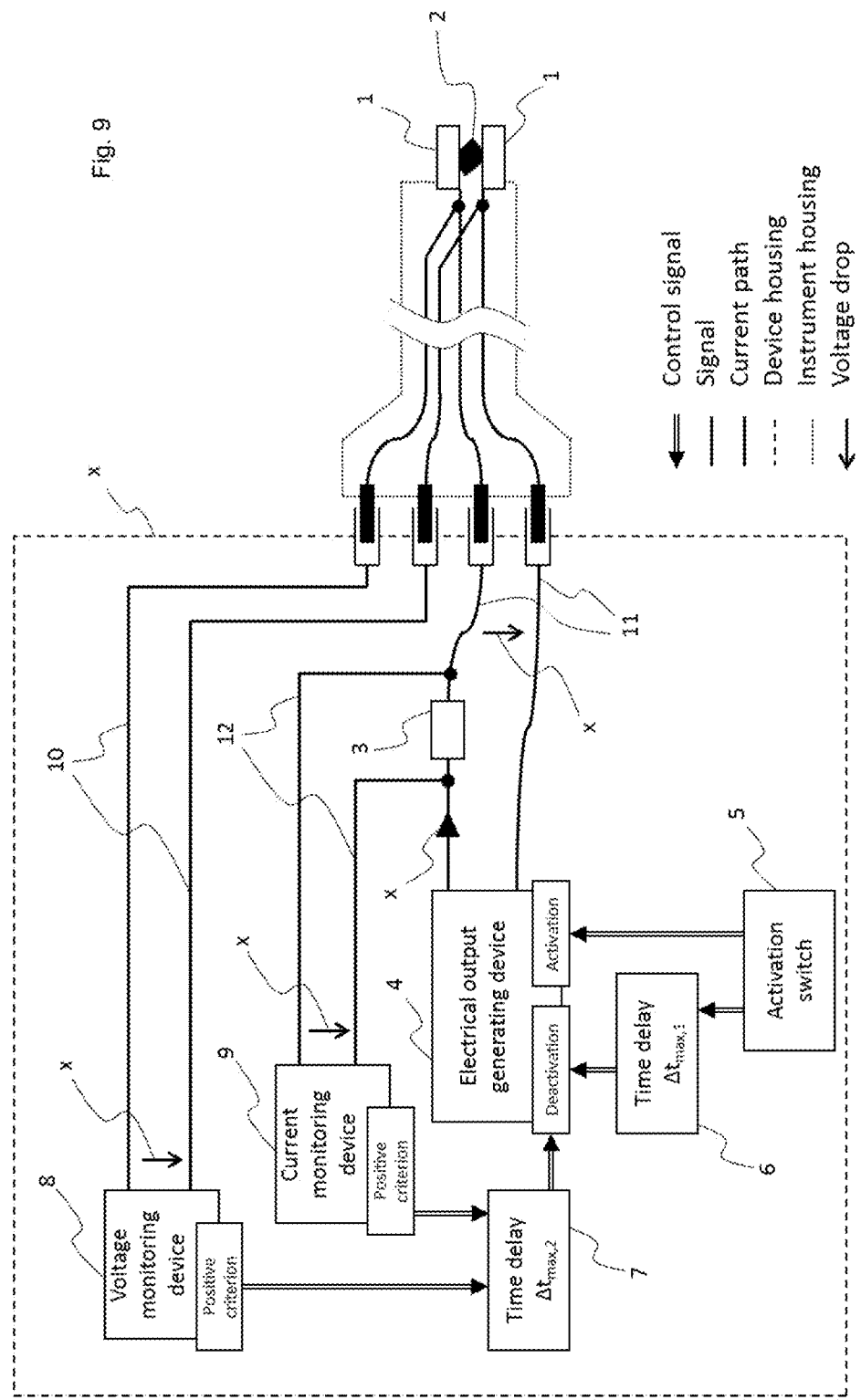

MEDICAL DC CURRENT GENERATOR AND BIPOLAR MEDICAL IMPLANT FRAGMENTATION DEVICE EQUIPPED THEREWITH

BACKGROUND OF THE INVENTION

The present invention relates to a medical direct current generator adapted to be connected to a surgical/medical cutting device, preferably according to EP 2967712 A1, for fragmenting thin-walled and/or wire-shaped metallic implants, with direct current.

PRIOR ART

For the description of the present invention, it is presumed that the teaching of EP 2967712 A1 is known, wherein this prior art document is made the subject matter of the present application.

In more detail, in EP 2967712 A1, a surgical/medical implant-cutting instrument of the bipolar type and operated with direct current is disclosed. This instrument has an instrument head which is located at the distal end of an instrument shank or shaft and which is adapted for minimally invasive insertion of the instrument into a patient's body preferably via an endoscope. The instrument head is equipped with at least two mutually opposing instrument branches, the positioning of which defines a cutting gap for receiving an electrically conductive implant or implant section.

Cutting is achieved by applying one or several single DC current pulses onto an implant segment after a physical contact between the branches and the implant material is detected. The application of a single DC current pulse onto the OTSC clip ("over the scope clip") material leads to very localized heating of a cross-section of the implant material (for example Nitinol) to its (well-known) melting point. The melting point, for example, of Nitinol is at approx. 1300° C. The DC current generator as well as the respective surgical/medical instrument have been designed in a way that the parameters of the DC current pulse are optimized for effective cutting at minimal collateral effects like electrolytic and faradic effects.

According to the instrument shown in the EP 2967712 A1, electrodes are formed on the mutually facing longitudinal sides of the branches or these are each equipped with at least one electrode each, wherein these electrodes are in turn shaped at their mutually facing longitudinal sides to form a cutting edge in order to effect a quasi linear or punctiform physical contact with the electrically conductive implant or implant section for an electrical short circuit between the electrodes.

The aim of the instrument design according to EP 2967712 A1 is to achieve melting of a particular volume of the implant material (between the electrodes) by using a minimal amount of electrical energy. This is achieved by establishing a small (pinctiform) contact area between the electrodes and the implant material, through which a high current density is achieved to ensure that only a very limited volume of metal is melted. Furthermore, the current pulse duration is minimized/limited in order to reduce heat dissipation effects. To be able to achieve melting of the implant material within very short pulse duration, a high current in the range of 150 A is required wherein a voltage value Of about 2 to 4V can be measured at the implant/electrodes. This instrument design allows for effective and very localized melting of a cross-section of the implant material substantially between the electrodes within a few milliseconds, typically between approx. 20 ms and 100 ms.

Now, the applicant realized that even if the above well-known medical instrument was correctly used the fragmentation success could not be securely achieved although the melting effect of the implant material occurred.

The applicant found out that at the point in time when the cross-section of the implant material is melted, there is a very high heat gradient along the implant material essentially perpendicular to the current flow through the implant material. This very high heat gradient obviously leads to a very high heat flow from the melted material section towards regions of cooler implant material, effectively away from the melted material in perpendicular direction with respect to the current flow between the electrodes.

Therefore, at the point in time when the cross-section of the implant material is melted, the heat dissipation in a direction that is essentially perpendicular to the current flow between the electrodes is at its maximum and leads to a very strong cooling effect of the melted material.

The cooling effect at the point in time when the very small implant material section is melted, however, leads to rapid cooling and therefore re-solidification of the melted implant material. This re-solidification can take place within approx. 50 up to a few 100 microseconds.

The applicant finally found out that at the point in time when a full cross-section of the implant material is melted, the implant sections on either side of said cross-section start moving due to forces exerted on the implant structure, e.g., from the contacting bipolar surgical/medical instrument, from surrounding tissue or due to tension within the implant structure. This movement sometimes led to an abrupt loss of physical contact between at least one electrode of the surgical/medical instrument and the implant material, and therefore to an abrupt interruption of the current flow. At this point in time when an abrupt interruption of the current flow took place, the strong heat dissipation led to a fast re-solidification of the implant structure, often before the implant section could effectively be separated/dissected. As a result, the fragmentation attempt was unsuccessful, as the overall implant structure remained intact.

Short Description of the Invention

In light of this problem recognized by the applicant for the very first time, it is an object of the present invention to provide a medical current generator of a surgical/medical cutting device and a surgical/medical cutting device being equipped therewith, operating on the basis of direct current, that is adapted to provide an electrical output after physical contact between cutting electrodes of a medical instrument of the cutting device and a medical implant (made of metal) is established for melting the implant material and that improves the fragmentation success even if the already melted implant material starts moving.

This object is basically solved by means of a direct medical current generator having the features of claim 1. Advantageous configurations are subject-matter of the dependent claims.

More concrete, in order to solve the above object the present invention provides a medical direct current generator and a surgical/medical cutting device being equipped therewith wherein the medical direct current generator has or is connected to a control device, for example a CPU or analogue control circuit having a first control portion (or implemented control process) being adapted to apply an electrical output/current after physical contact between cutting electrodes of a medical instrument of the cutting device and a medical implant (made of metal) is established for melting the implant material and a second control portion (or implemented control process) being adapted to maintain the current flow through the implant material after a (abrupt) loss of the physical contact between at least one electrode and the implant material preferably for a predetermined time, wherein the predetermined time is adjusted or pre-adjustable preferably on basis of a plurality of tests with different implants/implant materials, to safely avoid re-solidification of the implant material before the separation/dissection of the implant segments is completed.

The present invention therefore discloses a medical DC-impulse generator which is adapted to be connected to a bipolar surgical instrument (or which is connected to the bipolar surgical instrument) and which preferably contains a current source which is adapted to apply a direct current of predetermined or adjustable strength (maximum current value in ampere) in a pulsed or timed way to the electrodes, such that a quantity of current (or energy density) in at least one current pulse is sufficient to melt an (already identified) implant material between the electrodes (preferably orientated to each other to generate a punctiform physical contact with the implant material), wherein the medical direct current generator (DC-impulse generator) preferably has the CPU or is connected to a CPU or another control device of this kind (for example analogue control circuit) which is adapted to determine and control the electric current flowing through the electrodes such that the performance of a two-phase cutting process is implemented in which the current pulse consists of two consecutive phases.

In the first phase during which the electrodes have (mechanical/physical) contact with the implant, the material of the implant between the electrodes is heated up (melting) by the current flowing from one electrode to the other electrode directly via the implant material (short circuit phase). This first phase is also called the heating (melting) phase. In the second phase, the electrical output of the current generator is adapted/controlled to allow/generate/keep an electric arc to extend between at least one of the electrodes and the implant material preferably for a predefined maximum duration/time period (electric arc phase) starting from the time point at which the interruption of the physical contact has happened/was detected. This second phase is also called cutting phase.

At the point in time when one electrode loses physical contact to the implant material for example, because the already melted implant material starts moving, the distance between the electrode(s) and the implant material increases gradually and allows an electrical arc to be established even at low voltages when/because the distance between said electrode(s) is very small (e.g. in the range of few micrometers). In air, the electrical field strength required to establish an electrical arc is approximately 1000 V per millimeter. Therefore, for example, at small distances in the range of about 1 micrometer, a voltage in the range of about 1 to 2 volt is sufficient to establish an electrical arc between two conductors (in this case: at least one electrode and the implant material). Therefore, in the first moments after interruption of physical contact between at least one electrode and the implant material, an electrical arc is established for the predetermined maximum time period.

Once established, the electrical arc represents its own conductive path and therefore does not require comparable electrical field strengths to maintain the electrical arc as are needed to initiate a new electrical arc. Therefore, the electrical arcs established after physical contact interruption between an electrode and the implant material can be maintained for a certain time with comparably low voltages.

Furthermore, maintaining the electrical arc requires the use of DC current, since only DC current provides a non-interrupted current flow. When AC current would be used, e.g. in Argon Plasma Coagulation (APC) application, an electrical arc is established and extinguished with each half cycle of the sine wave. Due to this, the voltage used in APC application is at several thousand volts, and an atmosphere that provides easy ionization properties is required. Furthermore, it should be noted that the present invention takes advantage of the maintenance of the appliance of electric current even after an interruption of physical contact between the at least one electrode and the implant material is detected such that an electric arc is generated maximal for a predetermined time period (or until the implant material is cut at an early time point), wherein the EP 2967712 A1 teaches to avoid an arc in any case for which the system being disclosed there can be/is equipped with a "shut-off" device.

The heating (melting) phase, which is the first phase of the pulse, is a monophasic rectangular waveform of typical durations from about $\Delta t=10$ ms to max $\Delta t=120$ ms. Preferably, the maximum pulse duration in that phase is about $\Delta t=60$ ms to max $\Delta t=100$ ms and more preferable $\Delta t=80$ ms (milliseconds). The duration of the heating phase can vary, since the moment in which a loss of physical contact between the electrode and the implant material takes place/is detected cannot be pre-determined and varies between individual current pulse applications.

Preferably a time lagging element is provided being adapted to assure that a predefined pulse duration is not exceeded. The time lagging element prevents the instrument from overheating, since the voltage drop over the high current wires between the current source and the electrodes is generally very big (more than 20 V) and the current is very high (more than 100 A).

During the heating phase, the electric current is essentially constant and set on a pre-defined value, preferably in the range of 145-155 ampere. Furthermore, the voltage between the electrodes (detected at positions close to the electrodes) is comparably low, typically in the range of 1-3 volt (wherein the voltage of the electric current source is about 36-48 volt). As soon as physical contact between at least one electrode and the implant material is lost and an electric arc is established (maximal for a pre-determined time period), the electrical arc represents a further component within the current path, the resistance of which is strongly fluctuating. Therefore, as soon as the electric arc is established between at least on electrode and the implant material, the current immediately decreases and fluctuates at a level considerably lower than the current value during the heating phase. Furthermore, the voltage between the electrodes immediately increases and fluctuates at a value considerably higher than the voltage value during the heating phase.

In order to be able to tailor the electrical output to the two consecutive phases, the medical DC current generator is adapted to detect an abrupt loss of physical contact between at least one electrode and the implant material during DC current application. This is preferably achieved by monitoring the voltage between the electrodes with a voltage monitoring device (voltage meter), or the current flowing from one electrode to the other electrode via the implant material with a current monitoring device (current meter), or both.

The cutting phase is a monophasic pulse, preferably with a maximal pulse duration of $\Delta t=50$ μs to 500 μs. A time lagging element limits the duration of the cutting phase to a predefined value. Preferably, $\Delta t$ is about 450 μs (microseconds). In this phase, the cutting process is achieved by an electric arc between at least one electrode and the implant.

The current control device in the present invention therefore may contain a safety device and a lagging element to control the duration of the two phases. In such a case the safety device is connected to a switch and the current source. The lagging element is connected to the current source. The lagging element maintains the current in the second (cutting) phase. When the current source is activated by the switch, the first phase of the cutting process and also a timer in the safety device are started. Preferably, the switch is a foot-switch.

The lagging element is electrically connected to the current source and adapted to maintain and limit the duration of the DC-current pulse in the second phase. The lagging element maintains a DC pulse for a predetermined time after activation.

The current flows from the current source via high current wires to the electrodes, between which the implant, being in electrical contact with the electrodes, is located.

A voltage drop over the electrodes/implant can be measured via the voltage control unit (voltage sensor/meter) (dU/dt), which is in electrical communication with the lagging element. If the voltage over the electrodes/implant exceeds a predetermined limit, the voltage control unit emits a signal (a "positive criterion").

The voltage in the first phase (melting phase) can be adjusted to about 2 V at the electrodes, depending on the current being fed through the electrodes, and the resistance of the implant between the electrodes. The "positive criterion" from the voltage control unit starts the lagging element. Additionally, when the voltage rises, the current source limits the voltage between the electrodes to approximately 4 V.

An independent current control unit (current meter) as a redundant control can be applied to control the current through the implant/electrodes/high current wires. The current control unit (current limiter) is in electrical communication with the lagging element. The current is measured for example as a voltage drop over a shunt, which is connected in series with the high-current wires and the electrodes.

If a change in current (dI/dt) is detected (the current drops from a high value to a low value), a signal can be emitted, similar to the signal emitted by the voltage control unit. This signal then also serves as a "positive criterion", as described for the voltage control unit, and can independently start the lagging element.

The "positive criterion" represents/indicates the moment when the material (metal) of the medical implant loses physical contact to the electrodes (metal is melted, first phase is finished) and the second phase, namely the cutting phase, starts. An arc between the electrodes and the melted metal is then formed when the electrodes lose physical/metallic contact to the implant.

This arc is maintained by the lagging element which was activated by the "positive criterion" and which is in electrical contact with the current source. If a predetermined time has passed (max. 600 μs) the lagging element deactivates the current source. Here, it shall be noted that the above predetermined maximal time can be found out, for example, by tests with difference implant materials and stored in the control device (memory portion as rom, memory stick or the like). Accordingly, different times for different materials could be stored in the control device or only one time can be used which guarantees cutting success for any material generally used for medical implants. In addition the maximal time for maintaining the electric arc after the loss of physical contact should be selected such that damages of a patient can be avoided.

When the metal is completely melted (exclusively in the contact area between the implant and the electrodes) and the electric arc has dissected the implant (exclusively in the area of melted implant material), the electric arc automatically collapses (even if the predetermined maximal time has not been expired) since there is no melted metal between the electrodes anymore. The distance between the electrodes becomes too far for the electric arc. This normally takes place during the time the lagging element maintains the current. The collapsing of the electric arc when the implant is dissected finishes the cutting phase. The safety device in any case deactivates the dissecting process after the predetermined time to avoid damage of tissue and overheating of the instrument. The safety device keeps the current source activated for no longer than 120 ms, preferably for no longer than 80 ms as the above-mentioned predetermined time for the electric arc.

A general energy consideration of "Metal Separation with DC Current" according to the present invention reads as follows:

The crystal lattice of a metal has a characterizing thermal energy which manifests itself in vibrations of the atoms of the lattice. Thermal energy is thereby a kinetic energy and thermal energy $E_{th}$ of a material depends on the temperature T, mass m and a material specific constant c (specific heat capacity):

$$E_{th} = c \cdot m \cdot T$$

A DC current running through the material leads to an increase of thermal energy $E_{th}$ (heating), which equals the electrical energy $E_{el}$ absorbed by the material. This electrical energy $E_{el}$ depends on the power P and the duration $\Delta t$ of the DC pulse:

$$E_{el} = P \cdot \Delta t$$

Both the thermal and the electrical energy are commonly specified by the units watt seconds (Ws) or joule (J).

When the current runs through the material, the electrical energy is completely converted into thermal energy, which leads to a difference in thermal energy stored in the material between $t_0$ and $t_1$. The temperature difference $\Delta T$ between the heating zone and neighboring material of the implant material leads to dissipation of energy. This energy $E_{Diss}$ is lost for increasing the temperature towards the melting point in the heating zone. The heat dissipation depends on material parameters, which are combined in the variable k and not specified further, as well as from the integral of the temperature difference over the pulse duration $\Delta t$:

$$E_{Diss} = k \cdot \int_{\Delta t} \Delta T(t) \cdot dt$$

The dissipation of thermal energy is strongly dependent on the pulse duration $\Delta t$: the shorter the pulse, the less thermal energy dissipates from the heating zone and is lost for reaching the melting temperature.

The difference in thermal energy $E_{th}$ at the beginning ($t_0$) and at the end ($t_1$) of the heating phase can be described as follows:

$$E_{th,t1} = E_{th,t0} + E_{el} - E_{Diss}$$

The temperature increase ΔT can be calculated as follows:

$$\Delta T = (T_{t1} - T_{t0}) = \frac{E_{el}}{c \cdot m} - E_{Diss}$$

Including the specific material density ρ and the volume V of the heating zone, this leads to the following proportionality:

$$\Delta T = \frac{1}{c \cdot \rho} \cdot \frac{E_{el}}{V} - k \cdot \int_{\Delta t} \Delta T(t) \cdot dt$$

Referring to the above proportionality, the material constants c, p and ΔT are given by the implant material. Hence, three parameters remain with which it is possible to optimize the DC pulse and therefore the cutting process:
 a) Increasing the electrical energy $E_{el}$ applied to the material
 b) Reducing the volume V of the heating zone
 c) Reducing the pulse duration Δt in order to reduce thermal energy dissipation A decrease of pulse duration Δt according to c) leads to a reduction of electrical energy $E_{el}$, which counteracts a). This can be compensated for by increasing the power P. Therefore, it is advisable to minimize the pulse duration Δt in order to reduce the amount of dissipated thermal energy $E_{Diss}$ and to maximize the electrical power P of the pulse in order to still apply enough electrical energy $E_{el}$ to the material within a short pulse duration.

In a preferred embodiment, the medical DC generator and/or the medical fragmentation device being equipped with the medical DC generator according to the present invention is preferably adapted such that the sum of the duration of the two consecutive phases as defined above is shorter than 120 ms, preferably equal to or shorter than 80 ms.

In a further preferred embodiment, the medical DC generator and/or the medical fragmentation device being equipped with the medical DC generator according to the present invention is adapted such that the second phase of the two consecutive phases has preferably a duration between 50 μs and 600 μs, preferably a duration of 450 μs.

Preferably, the medical DC generator and/or the medical fragmentation device being equipped with the medical DC generator according to the present invention is designed to cut and/or fragment so-called over-the scope-clips. The medical DC generator and/or the medical fragmentation device being equipped with the medical DC generator according to the present invention can alternatively be adapted to cut the wire of metallic stents by the use of specific electrode forms. In that case, the branches/electrodes are formed to be line-shaped, so that the single wire of a stent can be grasped in a better way than with a point shaped electrode.

The DC-impulse generator, which is used in the implant cutting or fragmenting device is equipped with an internal energy storage device or energy buffer which can store and release a short high power pulse. Energy buffers can only be realized by charging DC power into energy storage units such as capacitors or batteries.

Considering the maximum specifications of, preferably, max. 26 V output voltage at the DC-impulse generator at max. 155 A output current, the output power, in case of DC current, is up to P=4030 W for a pulse duration of max. Δt=120 ms. This, in other words, means that the average output power over a time of 1 s is more than 480 W (483.6 W). This is an additional reason for providing the safety device, namely to avoid overheating of the instrument.

To draw a power of 4030 W for 120 ms directly from supply mains may be not feasible. Therefore, said energy buffer is charged over a longer time from a supply mains (the DC-impulse generator requires approx. 10 min for initial charging), which allows discharging with high power for a short time without sourcing from the supply mains.

Additionally, DC current is the favorable solution in this case. The medical DC generator and/or the medical fragmentation device being equipped with the medical DC generator according to the present invention is less complex and technological requirements also reduce risks associated with failures. Drawing AC power from a DC energy buffer would significantly increase technical complexity of the device. In the case of AC output, the amount of energy required for cutting is higher than in the case of DC output. The technical requirements on an energy buffer and DC to AC converters is further increased.

Preferably, the energy storage device is a capacitor of the high-capacitance type, preferably a "Gold-Cap" capacitor or an "Ultra-Cap" capacitor. Preferably, the capacitance of the storage device is greater than 15 farad. The energy storage device allows the device to generate a DC pulse without additional load on the power supply.

The DC current impulses, which are generated by the DC-impulse generator and which are applied to the mutually opposing electrodes between which the cutting gap is formed, have a current strength of more than 100 amperes, preferably between 140-155 amperes, In a further embodiment, the device is construed such that the two instrument branches are movable or settable via an actuating mechanism in order to change the cutting gap width in a defined way.

Also according to the present invention, a method for endoscopic cutting/fragmenting metallic implants is disclosed, which comprises the following steps:

In a first step of the method, a metallic implant is physically contacted with at least two electrodes preferably at the tip/head of an instrument shaft, so that the material (metal) of the implant is positioned between the electrodes like a resistor between two poles. The electrodes have an outer shape (needle or knife-shaped), respectively to realize a physical contact area between electrode and material (metal) of the implant which is nearly point-shaped or linear-shaped (one-dimensional).

In a second step, a current pulse of predetermined strength is applied from the DC-impulse generator to the (metallic) implant in the first phase of two consecutive phases, so that the metal of the metallic implant melts in the area between the electrodes. The pulse duration in the first phase can be found out by tests in accordance with the selected predetermined pulse strength (current value).

The current control device (for example CPU) is adapted to determine a current-flow through the implant (when physical contact is established) preferably via a shunt which is switched in series with the implant, wherein (in a third method step) the current control device detects the current flow through the material of the medical implant and the electrodes during the first phase ($t_0$-$t_1$).

In a fourth step, when detecting a current drop to a reduced level at ($t_1$), the current-flow in a second phase ($t_1$-$t_2$) is maintained at that reduced level (for at least a duration of 50 μs to 500 μs, preferably for a duration of 450 μs, but not exceeding 600 μs) to ensure that the implant material having already melted when physical contact is established is (completely) separated with an electric arc, being generated by the reduced current level. The current drop at ($t_1$) is detected by the current control device in the DC-impulse generator.

Furthermore, a DC-impulse generator with a current control device is provided which is adapted to generate current pulses to carry out the above-described method. The pulse generator is further adapted to deliver these pulses to contacts to which conductors or electrodes can be/are attached.

In general, the invention is based on the following considerations:

In order to avoid tissue damage, even in the absence of a special protection (or cooling) device, the heat input into the implant material to be dissected should be as small as possible and yet lead to fast melting of the implant/stent material.

This can be achieved by keeping a contact surface/touching surface between electrode and the stent material as small as possible (preferably punctiform), in order to obtain a high current density in the physical contact region/transition (in the case of direct application of a direct current).

That is, the active contact surface/touching surface is configured by at least one electrode in a way that the highest current density is achieved along the entire electrical current path. This is achieved by the at least one electrode (or the electrodes at both branches) having a region provided for the contact engagement with the implant, which shows or defines an (essentially one-dimensional) point-shaped (or line-shaped) contact, which is well achieved by a circular contact. Preferably, the electrode has a convex or knife-like shape. The implant material heats up at this contact location which has a very small surface, particularly due to the high current density, and is thereby quickly melted before the implant material located further away starts to heat up. For this purpose it has turned out to be particularly advantageous when at least the electrodes are made from a heat resistant material, such as a low-alloy steel or especially from metals like copper, wolfram or silver.

Additionally, the heat input should take place by direct application (with physical contact between the electrodes and the medical implant) of an electric direct current, wherein the electric direct current is pulsed or cycled. Each resulting DC packet causes thermal energy input into the metallic material of the implant or stent material, wherein the heat dissipation into the surrounding tissue is nevertheless small (in comparison to a non-cycled application of current) due to the inevitably short impulse duration.

The electrodes of the bipolar instrument according to the invention can additionally or alternatively be arranged at the instrument tip such that the instrument itself deploys a sort of protective effect without having to arrange a specific protection device according to prior art. For this purpose, the formation of two instrument branches extending in the longitudinal direction of the instrument, forming between themselves a (longitudinal) cutting gap, with the instrument branches possessing electrodes or forming electrodes at their respectively facing sides, has been shown to be advantageous. Therefore, the electrodes can inevitably turn away from the surrounding tissue, wherein the branches arrange themselves shieldingly between the electrodes and the surrounding tissue.

In order not to damage the surrounding patient tissue, it would be advantageous if DC current impulses of high current strengths (more than 100 amperes, preferably between 140-155 A), are applied in fractions of a second and by means of control technology to the mutually opposing electrodes between which the weld gap is formed. The metal of the implant is thereby melted and cut between the electrodes without excessively heating up the implant material in the vicinity of the cutting gap. The reason for this, as was already indicated above, is that by means of current pulsing, the heat dissipation effect from the medical implant or stent into the surrounding tissue can be reduced. The voltage may thereby lie far below a limit of 48 volts for a low voltage, which is completely harmless for the patient (biocompatible).

The invention will now be explained in more detail below with reference to preferred embodiment examples with reference to the accompanying drawings.

FIG. 1 shows an illustration of a typical DC pulse of a medical implant cutting/fragmentation device according to the present invention, consisting of a heating phase ($t_0$–$t_1$) and a cutting phase ($t_1$–$t_2$), FIG. 2 shows the DC-impulse generator and accessories and a magnification of the tip of the medical implant fragmentation device according to the invention, FIG. 3 shows a table with specifications of different materials, FIG. 4A shows a schematic depiction of the material specifications along the current path and specifically the relevant segments of the DC cutter;

FIG. 6 shows the conceptual construction of two instrument branches at the distal instrument head of the device in physical contact engagement (short circuit engagement) with an electrically conductive implant.

FIG. 8 shows the current control device of the medical implant fragmentation device according to the invention.

Figure 1:
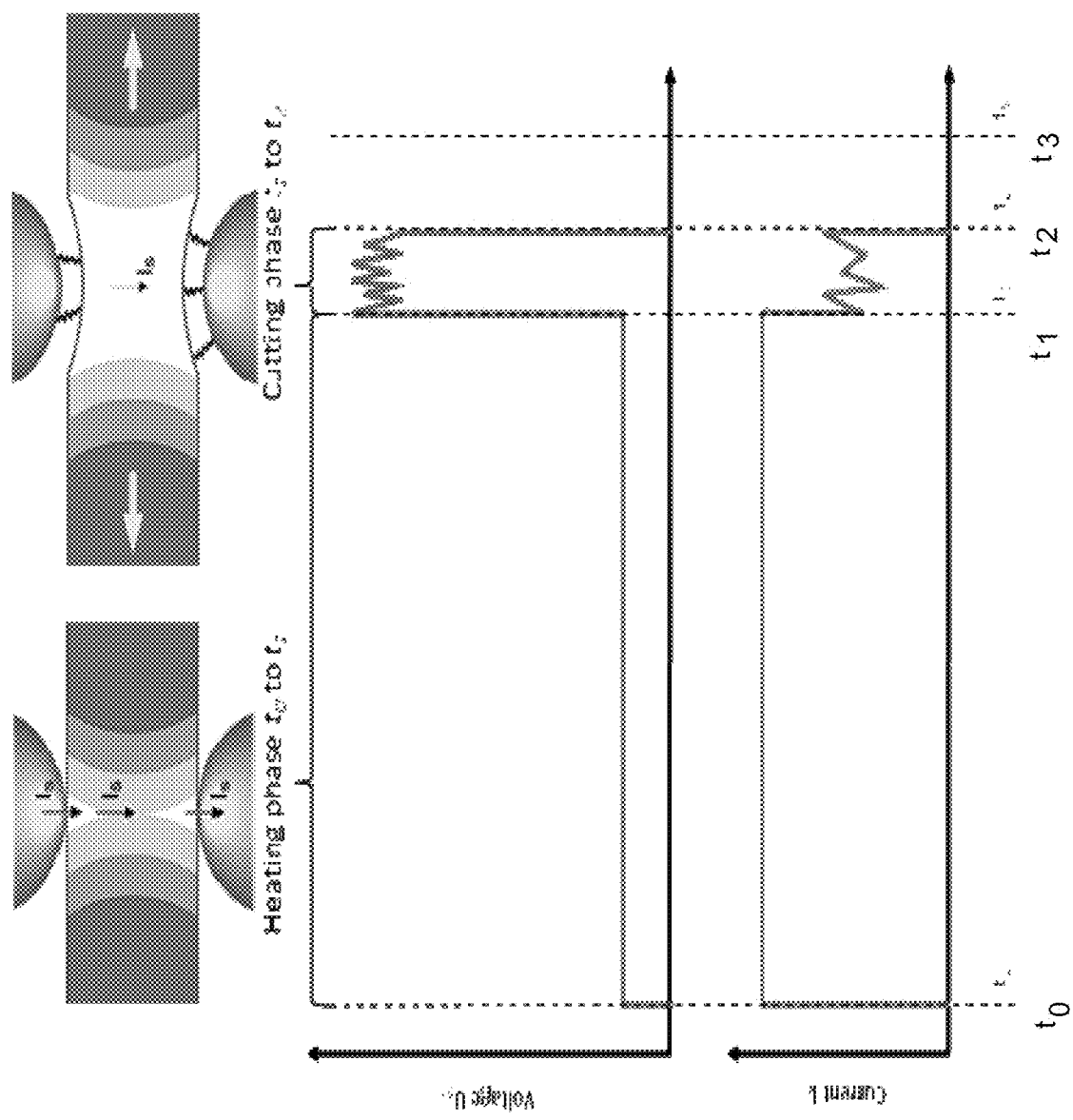

As shown in FIG. 1, according to the present invention at $t_0$, a DC impulse is released when two distal electrodes of a surgical instrument of the medical implant fragmentation device, represented by two semi-spherical elements 1, are in physical (punctiform) contact with an implant (stent) 2 being sandwiched by the two electrodes 1, wherein melting of the implant material in the contact area between the two opposing electrodes 1 and the implant 2 starts (first/melting phase). In case of an interruption of direct (physical) contact between at least one of the electrode 1s and the implant/stent material (at $t_1$), for example because of a movement of the already melted implant material, electric arcs between the electrodes 1 and the implant/stent material arise and maintain an electrical connection between the electrodes 1 and the implant/stent (second/cutting phase). These electric arcs lead to an abrupt increase of the voltage $U_{Gr}$ between the electrodes 1, and at the same time to an abrupt decrease of the current $I_S$. Both the current $I_S$ and the voltage $U_{Gr}$ become noisy signals during the second/cutting phase due to the instability of the current conduction through electric arcs (the electric arcs are unpredictably "dancing" within the space between the electrodes 1 and the material of the implant 2, much like the electric arc generated in argon plasma coagulation).

The figures are only illustrative drawings; diagram axes are not to scale. Nevertheless, it shall be clear from FIG. 1 that the subsequent second/cutting phase is much shorter than implied by the illustrative diagram (second/cutting phase is about 3 orders of magnitude shorter than the first/melting or heating phase). At $t_2$ at the latest (or even earlier), the electric arc finally collapses since the material of the implant 2 has been separated and the distance between the two opposing electrodes 1 becomes too large to maintain the electric arc.

It shall be noted here, that the current value and the voltage value during the above-mentioned first phase is held (adjusted) at a level being sufficient to melt the material of the implant 2 exclusively in a physical contact area between the two opposing electrodes 1 because of a short circuit therebetween. Preferably, the current source is controlled or selected such that a maximum current value of about 150 A and a voltage value of 36 to 48V is generated, which leads to a voltage value at the electrodes of about 2V. At the time point at which the physical contact gets lost, the current value drops and the voltage value rises automatically. However, according to the present invention, during the above-mentioned second phase directly following the first phase current value is (automatically) held (adjusted) at a level just being sufficient to generate/keep the electric arc between the electrodes 1 and the material of the implant 2. This can be done by a current control or by the respective selection of the suitable current source. Preferably, the voltage value at the electrodes rises up to about 4V (because of the limits of the selected current source or its control) wherein the current value adjusts itself respectively because of the generated electric arcs.

Furthermore, the maximal duration of the second phase is selected to be about 500 μs in this preferred embodiment which maximal duration is pre-selected based on tests with different implants/implant materials substantially guaranteeing the cutting success but also the protection of the patient, It shall be clear here, that the duration of the second phase could be shorter than the preferred maximal 500 μs because of an earlier cut of the implant.

Figure 2:
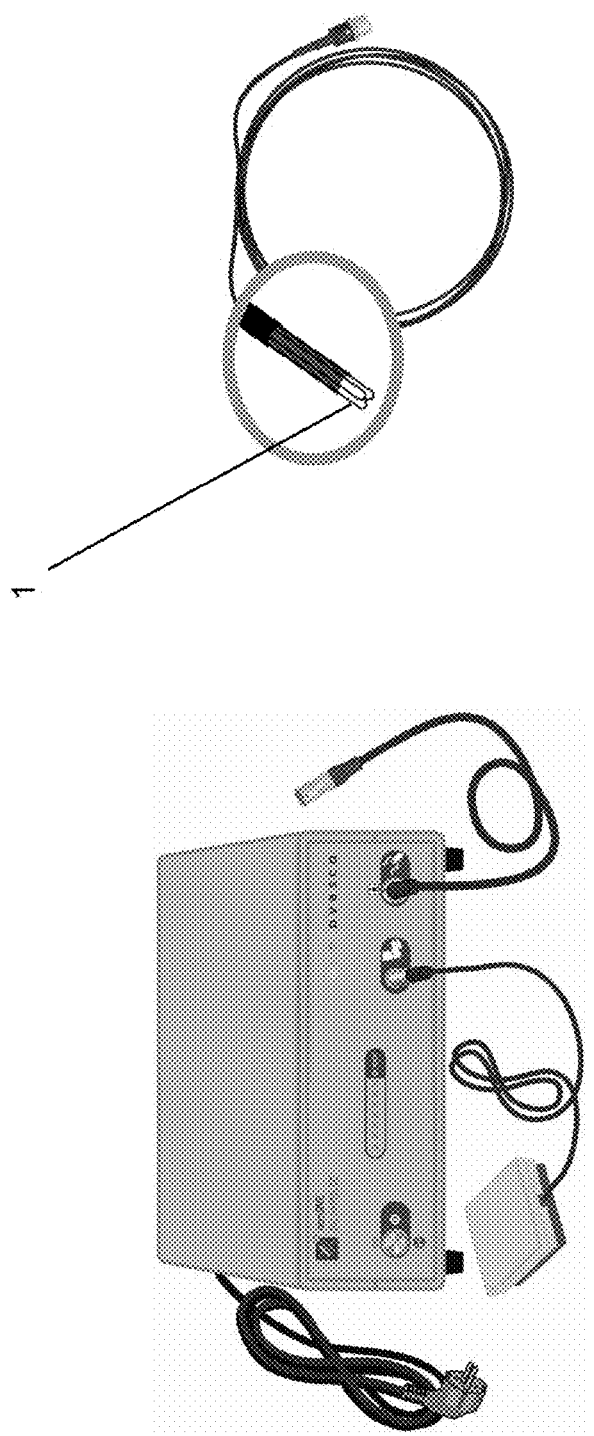

The medical implant fragmentation device in FIG. 2 represents an example for fragmentation of stents, such as tissue clips in the digestive tract. In order to be applicable with conventional flexible endoscopes, gastroscopes and colonoscopes, a cutting instrument (instrument shaft adapted to be introduced into the working channel of a well-known endoscope and having a distal instrument tip being equipped with the two opposing branches 2 as shown in FIG. 1) preferably has to have a length of min. 220 cm and a diameter of max. 2.6 mm. The DC pulse generated by a DC-impulse generator as shown in FIG. 2 must be conducted through the instrument shaft to the tip and back again, which leaves a total conductive length of min. 440 cm (2×min. 220 cm) for the DC pulse. Considering a required isolation and at least two additional sensing wires (as shown in FIG. 8), the (copper) cross-section available for conducting the DC pulse is not more than 2.5 mm² per single wire (i.e. 2.5 mm² over 440 cm).

The medical implant fragmentation device is a bipolar device with at least the two electrodes 1 provided in/at the two instrument branches at the distal end of the instrument shaft shown in FIG. 2. In case of three electrodes 1 (for improved gripping), two of the three electrodes have the same polarity). The instrument shaft contains at least four, preferably six conductive wires 10, 11, 12 as shown in FIG. 8:

two wires 11 for high current (large cross-section) connected to each one of two poles, and
at least two low diameter wires 10, 12 for voltage and/or current sensing, respectively, connected to one of the two electrodes 1 (poles) and/or a shunt 3.

The sensing wires 10 are required since the voltage decrease along the high current wires (about approx. 25 V along the entire high current path). The voltage, which is measured at the instrument tip, varies from approximately 2 V during the melting phase of the stent (first/melting phase $(t_0-t_1)$) to approximately 4 V. Approximately 4 V are measured when the second phase (second/cutting phase, $(t_1-t_2)$) starts. The current source in the DC-impulse generator then (automatically) tries to maintain the current, when the material starts melting and the electrodes lose contact to the melting metal. In trying to maintain the current, the current source shows the tendency to increase the voltage. To avoid a voltage which is too high and therefore dangerous for the patient, the voltage at the electrodes 1 is limited to approx. 4 V during the second phase.

The DC-impulse generator is designed to send an electrical direct current through the bipolar, surgical instrument. This DC pulse flows through the clip segment/stent/implant, wherein the two opposing electrodes 1 at the distal tip of the instrument are establishing physical contact with the implant 1 (see also FIGS. 6 and 7), resulting in localized heating and melting of the implant material. The DC-impulse generator delivers a direct current pulse of preferably optionally between 100 A-150 A.

The instrument branches are basically spaced or spaceable such that a cutting gap inbetween has a gap width which permits/ensures an introduction of an implant or implant section 2 (OTSC (Clip) or stent wire) into the gap when coming into physical contact with the two mutually opposing longitudinal branches/electrodes.

Now, if a metallic implant or an implant section 2 is introduced into the gap, generally the implant material already at the distal end portion of the instrument branches comes into contact with the respective electrodes 1 and short-circuits them, whereby, because of the applied electric current, the implant material between the electrodes 1 is heated and melted.

The contact resistance between the electrodes 1 and the implant 2 should be as high as possible in order to securely melt the implant material (exclusively) in the contact region (i.e. from the outside to the inward), but additionally to leave implant regions further away to be unheated as much as possible.

The energy input into the implant material should take place such that heat dissipation into the surrounding patient tissue remains as small as possible, even in the absence of additional protection measures.

Melting of one volume element of implant material by DC current can be calculated as follows:

The thermal energy $E_{th}$ that is required to melt one volume element of a material depends on the starting temperature $T_0$, the specific melting temperature $T_S$, the specific heat capacity c and the specific weight p:

$$E_{th} = c \cdot \rho \cdot V \cdot (T_S - T_0)$$

Given that $T_0 = 38°$ C. and one volume element V is 1 mm³, the values for the required melting energy per mm³ calculate as given in FIG. 3.

The disposition of a material to convert electrical energy into thermal energy is proportional to the ohmic resistance of the material. In order to consider this for the case of the present invention, where the same current $I_S$ runs through different materials, the specific melting energy is adjusted by the ohmic resistance (by multiplication with the reciprocal value of the specific ohmic resistance). This calculates a value, which allows for comparing different materials regarding their individual willingness to melt at a given current, and therefore regarding their suitability for being used in the current path of the present invention.

A relevant value for material selection (considering only electrical properties) is the resistance adjusted specific melting energy e. The aim of this selection is to maximize the difference between the material to be melted (the implant material) and the material used in the DC cutter instrument, in order to achieve very selective melting of the implant material, while the material used in the DC cutter instrument does not come even close to its melting temperature. The resistance adjusted specific melting energy is constant for a material and calculates as follows:

$$e = c \cdot \rho \cdot V \cdot (T_s - T_0) \cdot \frac{1}{r}$$

with the following variables:
e resistance adjusted specific melting temperature
c specific heat capacity
ρ specific weight
V volume element (here: V=1 mm³)
$T_S$ melting temperature
$T_0$ temperature before energy intake (here: $T_0$=38° C.)
r specific ohmic resistance An overview over relevant specifications of materials is given in FIG. 3.

Although copper has the highest resistance adjusted specific melting energy e, silver has been chosen as electrode material due to its biocompatibility. Consequently, the conductive wires inside the instrument shaft are made of copper, as they do not come in contact with the patient's tissue.

Figures 4A, 4B, 4C, 4D:
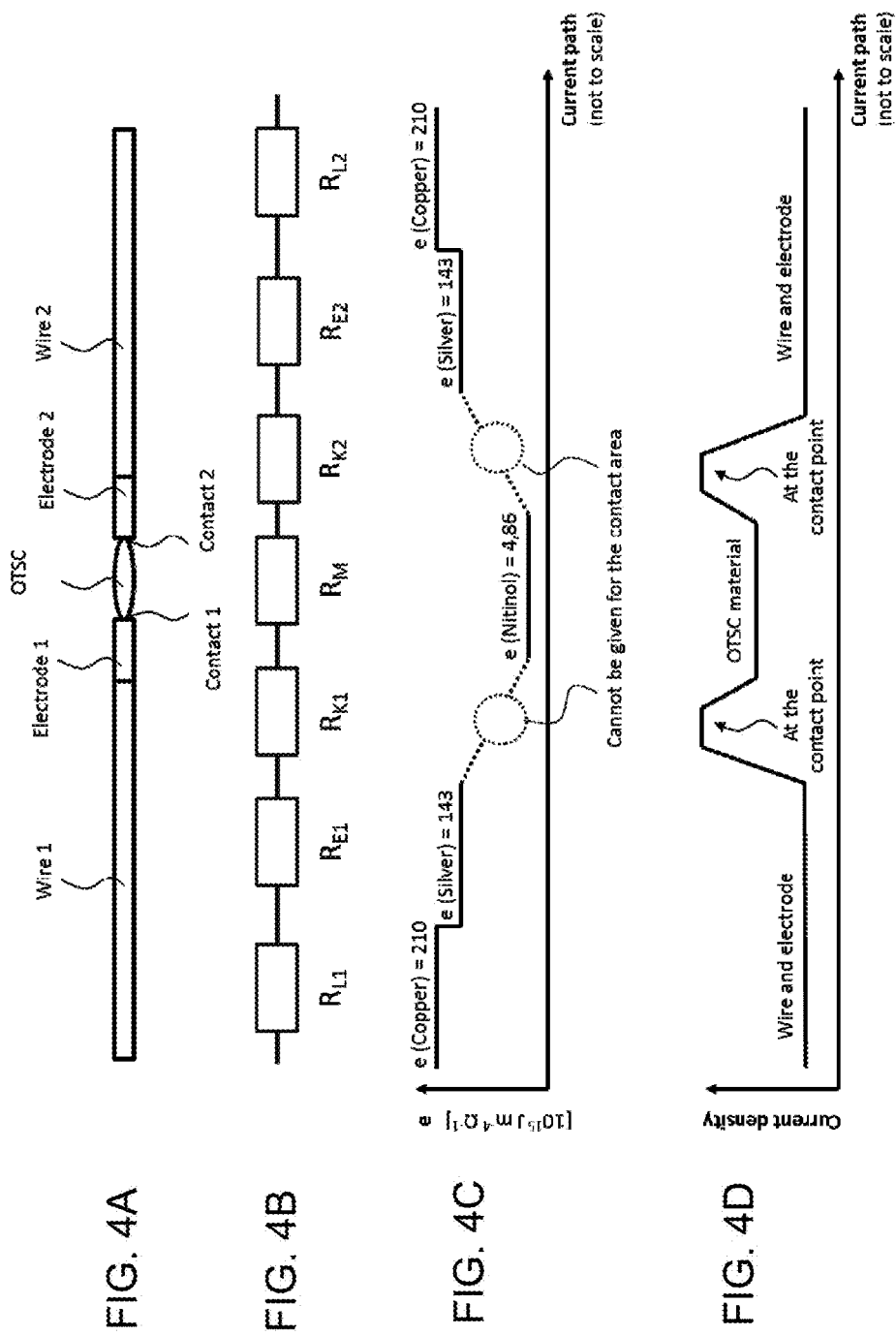
FIG. 4B shows a schematic depiction of an electrical equivalent circuit.
FIG. 4C shows the resistance adjusted specific melting energy along the current path.
FIG. 4D shows the current density along the current path

Material specifications along the current path of the DC cutter are given in FIG. 4. The upper schematic constructive illustration shows the relevant segments of the DC cutter. Below, an electrical equivalent circuit is depicted. The third diagram shows the "resistance adjusted specific melting energy" along the current path. A fourth illustrative diagram shows the current density along the current path.

With the material selection in FIG. 4, the relation of the resistance adjusted specific melting energy e of the implant material (Nickel-Titanium) and the adjacent electrode material (silver) is 4.86 vs. 143. This means that the tendency of the implant material to melt at the given current is 29.4 times higher than the tendency of the electrode material to melt. This provides a large safety margin and ensures that the electrode material does not heat up close to melting temperature, while the implant material reaches melting temperature much faster. Additionally, the wire material has an even higher resistance adjusted specific melting energy e of 210, thus the tendency of the wires to melt is even lower than the one of the electrodes.

Figure 5:
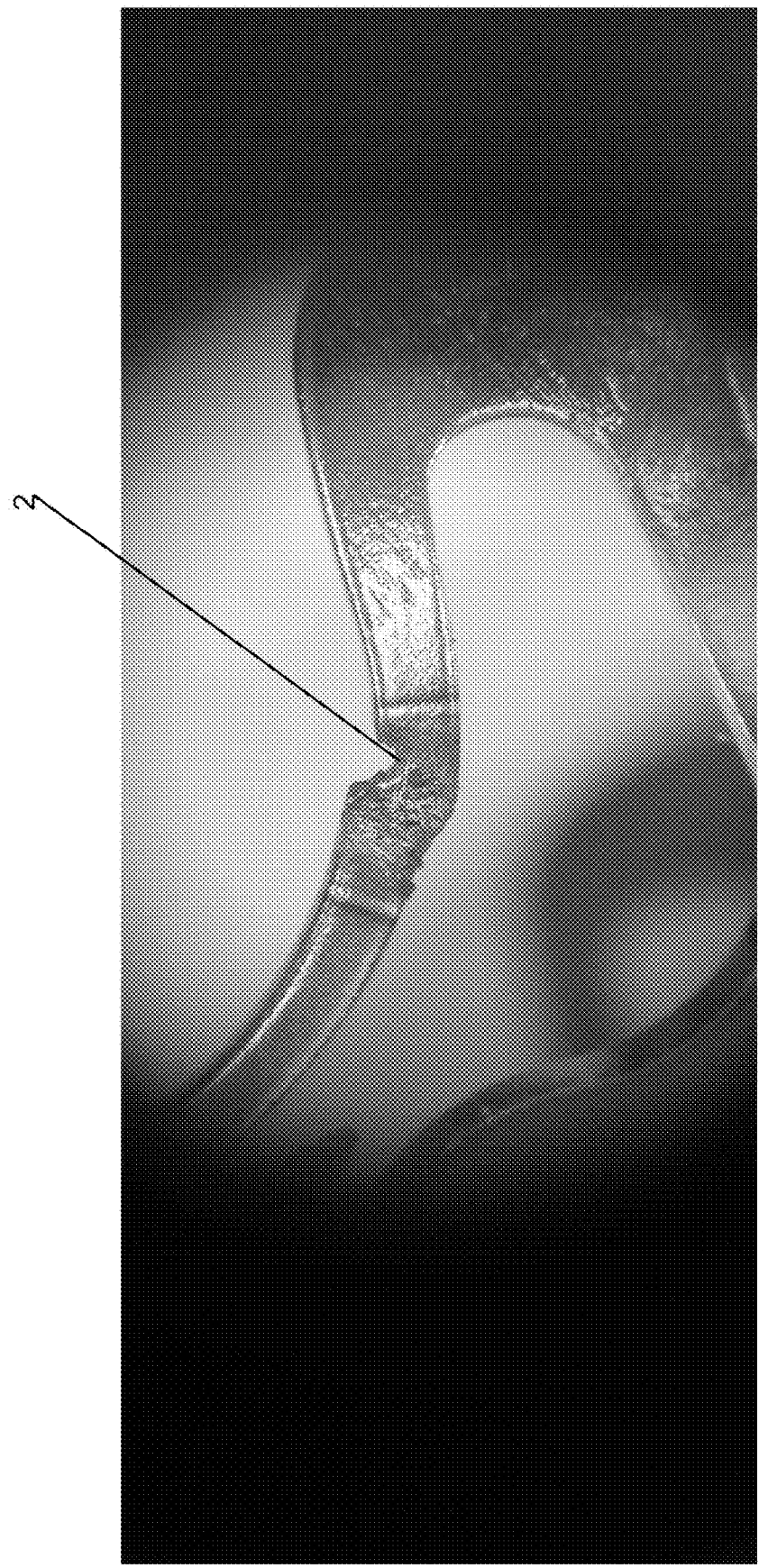
FIG. 5 shows an example for a re-solidified implant segment.

FIG. 5 shows an example where an implant segment has re-solidified after unsuccessful heating to melting temperature. During the heating phase (first phase as shown in FIG. 1), the material of the medical implant 2 in the heating zone reaches melting temperature; this temperature must be maintained for a short time in order to allow the implant segment to separate before the melted region (about the contact region between the electrodes and the implant) solidifies again. However, during the first phase separation of the segment cannot be safely achieved for the implant as shown in FIG. 5. In order to avoid re-solidification of the melted material (after losing physical contact between the electrodes 1 and the implant 2 especially because of movements of the already melted implant material), and to ensure effective separation of the implant segment, the cutting process according to the invention comprises the above mentioned second/cutting phase after the heating/melting (first) phase: The cutting phase which supports the cutting with an electric arc, has an abrasive effect on the melted material. Since medical implants generally have elastic properties (pre-tension), these properties normally support the fragmentation of the material when melting. In case the current pulse (during physical contact) is not sufficient (until the physical contact interrupts), the implant material cools down after melting, and the supporting elastic characteristic of the implant 2 is lost or at least reduced. No/low pre-tension is left in the implant material and it is very hard to fragment this re-solidified implant 2 again. This can happen if a medical cutting instrument according to EP 2967712 A1 is used. The additional abrasive electric arc, which is produced in the second (cutting) phase in the present invention, however, overcomes this drawback.

In FIG. 6, the punctiform physical contact between the implant material and the electrodes 1 is shown. Additionally, it can be seen, that a leakage current $I_L$ occurs if both poles/electrodes 1 of the DC cutting instrument of the bipolar medical implant fragmentation device are in direct contact with adjacent tissue.

The DC pulse current $I_S$ (specified to max. 155 A) is fed through the implant and generates a voltage drop $U_{Gr}$ between the electrodes 1. This voltage drop leads to the leakage current $I_L$ being fed through the tissue (if the electrodes 1 are in physical contact with tissue) and is a reason for limiting the voltage in the second/cutting phase. The leakage current $I_L$ spreads over the adjacent tissue, while the current density J decreases with increasing distance to the electrode pair. The current density J depends on electrode spacing and distance to the electrode pair as well as on the total leakage current $I_L$. In the consideration of the DC pulse current for cutting, $I_L$ is not considered, since $I_L$ is lower than $I_S$ by several orders of magnitude.

Figure 7A:
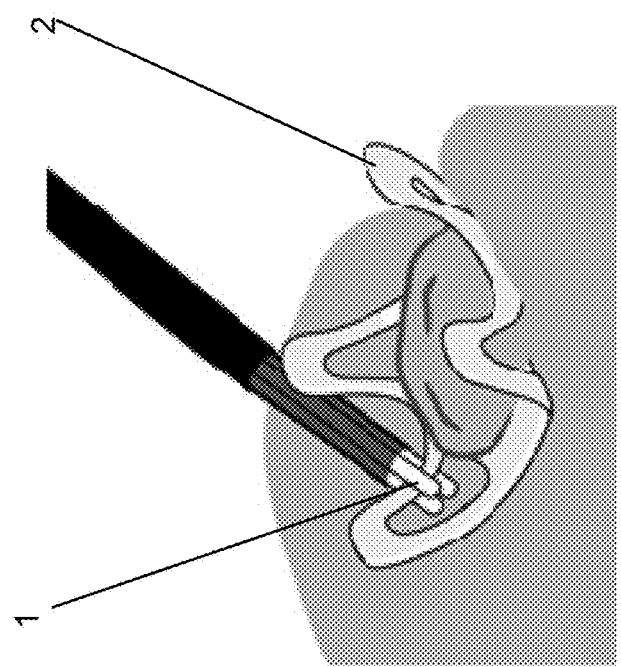
FIG. 7A shows the establishment of contact between an implant segment and the medical implant fragmentation device according to the invention.
Figure 7B:
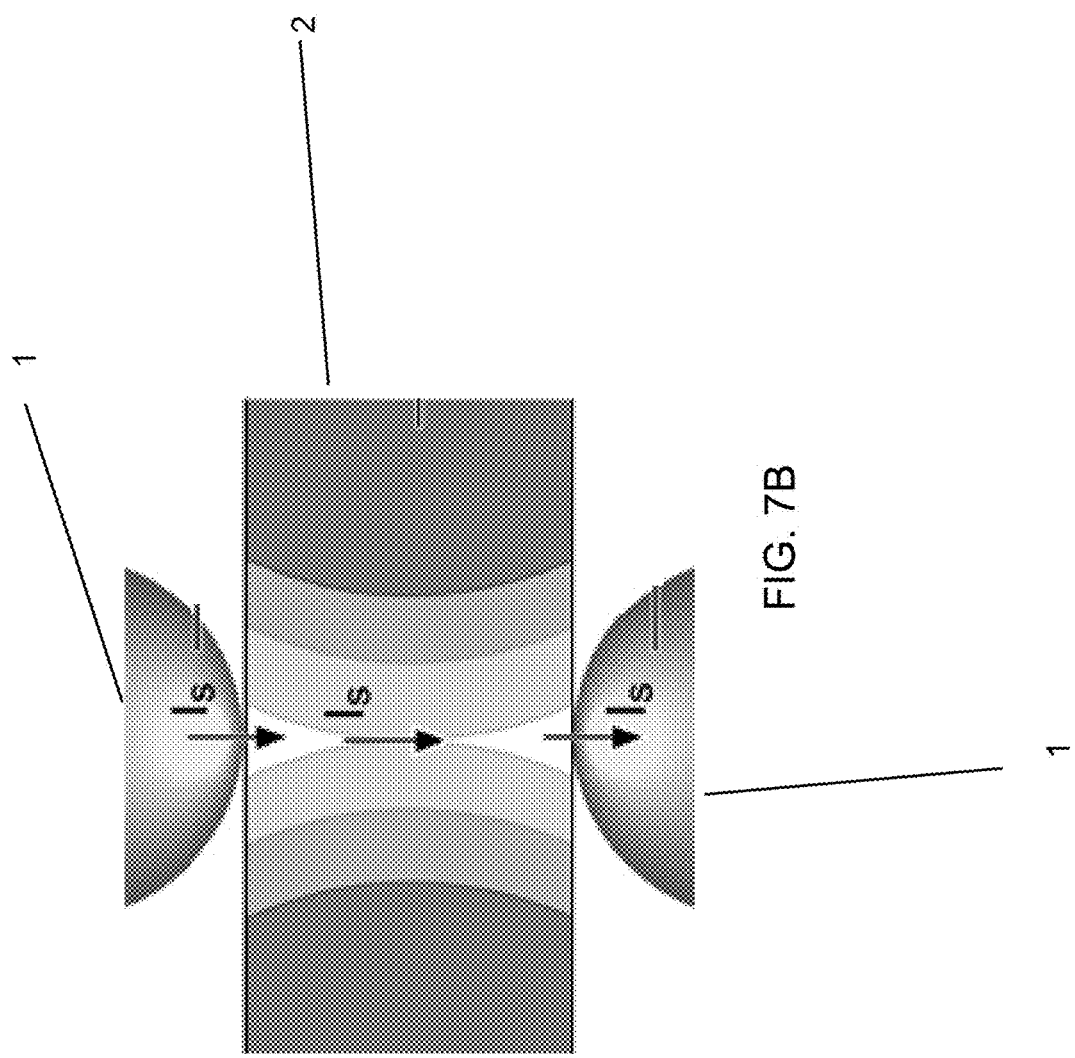
FIG. 7B shows a cross-section of an implant segment to be cut and marking of current path between electrodes.

In FIG. 7, the left drawing shows how a physical contact between an implant and DC cutting instrument is established. The right drawing shows the cross-section of an implant segment 2 to be cut and marking of current path $I_S$ between electrodes 1.

In FIG. 8, the control or working mechanism of the DC-impulse generator is shown in a block diagram and described in detail in the following.

The implant 2 is situated between the electrodes 1. The electrodes 1 are in electric contact (physical contact) with the implant 2. The electrodes 1 are further connected to the current source 4 via the two high current wires 11. The current from the current source 4 flows through the wires 11 to the electrodes 1 and therefore also through the (metallic) implant 2 to heat it up and melt the implant material. The shunt 3 is connected in series with one of the wires 11, which means that the current flowing through the implant 2 to melt it also flows through the shunt 3.

First ends of the two sensing wires 12 are connected to a first and a second end of the shunt 3, second ends of the sensing wires 12 lead to an unit 9 for current control. This current control 9 also measures the voltage drop over the shunt 3 when current is flowing through the wires 11. This voltage is proportional to the current flowing through the wires 11 and the implant 2. A first end of the sensing wires 10 is coupled to a distal end of the wires 11, respectively, preferably to the electrodes 1. A second end of the sensing wires 10 is connected to the voltage control unit 8, respectively.

If an activation switch 5 (e.g. a foot switch) is activated, the current source in the DC-impulse generator is activated. At the same time a safety device 6 is activated. The safety device 6 defines the maximum time the current source 4 is activated. The maximum time up to which the current source 4 remains active is defined as 120 ms, but preferably the current source 4, and therefore the DC-impulse, is deactivated after 80 ms. The reason being that the long wires 11 cause a large voltage drop over the wires 11. In connection with the current flowing through the wires 11, the wire material has to bear a power load of over 4 kW. It is clear that this would heat up the wires 11 and, in connection, also the complete instrument.

When the current flows through the wires 11, the current control unit 9 and the voltage control unit 8 detect a voltage and a current curve. The voltage curve is measured parallel to the electrodes 1, the current curve is measured via a voltage drop over the shunt 3.

When the current source 4 is activated via the activation switch 5, the metallic material of the implant 2 is in physical contact with the electrodes 1. The implant material (metal) is heated up and starts to melt. If the material melts, it loses contact to the electrodes 1, since the material "pinches" and an arc is formed between the electrodes 1 and the melted material (metal) of the implant 2. In other words, the melting material loses its form and does not physically contact the electrodes anymore.

In this moment, when the electrodes 1 lose contact to the material/metal of implant 2, an abrupt change in current and voltage occurs. Since this process takes place in fractions of a second, this is preferably measured by two instances: course of the current and course of the voltage. The current control unit 9 as well as the voltage control unit 8 can both emit a signal due to a "positive criterion" after current/voltage measurement. This means, that the current control unit 9 emits the signal according to a dI/dt measurement. If the electrodes 1 loses physical contact to the material/metal of the implant 2, the current strength in the wires 11 drops.

More or less simultaneously, the voltage, which is measured preferably at the electrodes 1 (the distal end of wires 11), rises from a first value to a second value. The voltage between the electrodes 1 during the first/melting phase (physical contact between electrodes and implant material/metal) is in a range from about 1.5 to 2.5 V, dependent on the current and the resistance between the electrodes 1 and the implant 2. The "positive criterion" for detecting a change in voltage is dependent on dU/dt (rising edge). Once the electrical arc starts at the beginning of the second phase (melted material loses physical contact to electrodes 1), the voltage between electrodes 1 rises and is preferably limited in a range from 3.5 to 4.5 V by the control device (or more concretely voltage control unit 8) of the DC current generator. Preferably, the voltage is (automatically) limited to a maximum value of about 4 V (biocompatible value) especially in the second phase. This is done in the current source 4 (DC current generator) and is necessary, since an ideal current source tries to maintain its load-independent direct current by rising its output voltage as high as necessary. This would most probably be dangerous for a human being.

Once the voltage control unit 8 detects the rise of the voltage, it emits a control signal, like the current control unit 9 does when detecting the drop of current at the wires 11. This starts the second/cutting phase.

The control signals of the voltage control unit 8 and the current control unit 9 are fed to a lagging element 7. This lagging element 7 is connected to the current source 4.

When the lagging element 7 is activated, the so-called "cutting-phase" ($t_1$-$t_2$) which has been previously mentioned in the description of the two consecutive phases, is maintained by the lagging element 7. The lagging element 7 can be programmed with different "time constants". The time constant defines how long the lagging element 7 allows the current source 4 to maintain the second/cutting phase. The maximum time constant in the lagging element 7 is about 600 µs, which is not exceeded. Preferably, the lagging element 7 maintains the second/cutting phase for 50 µs to 500 µs.

The choice of the timings is caused by the compromise between the "faradic effect" and cutting efficiency. Generally it can be said, the higher the lagging time is, the higher is the cutting efficiency, but also the risk caused by the faradic effect. The lower the lagging time, the lower the risk of the faradic effect, but at the same time the cutting efficiency decreases.

The duration of the time constants is a good compromise between the faradic effect and the electrolytic effect.

If, for whatever reason, the lagging element 7 is defective and is about to maintain the cutting phase for too long, the safety device 6 assures that the complete process time (melting phase 1+cutting phase 2) does not exceed 120 ms. Preferably, the current source 4, or rather the DC-impulse has a maximum length (start to stop) of not more than 80 ms.

To summarize the above explanation, the present invention is generally directed to a medical endoscopic implant cutting and/or fragmenting device of the bipolar type, operating on direct current, comprising an endoscope instrument being adapted to be inserted into the working channel of an endoscope and having at least two opposing electrodes at its distal instrument head forming a cutting gap inbetween for receiving an electrically conductive implant or implant section to generate punctiform physical contact with the implant, and a DC-impulse generator having or connected to a control device adapted to generate a direct current in a pulsed way being controlled by the control device such that in a first phase of physical contact, the current pulse is adjusted preferably by controlling the current value at the electrodes to induce electric energy into the implant material being sufficient to melt the implant material exclusively in the area of the contact portion and in a second phase of physical noncontact, the current pulse is continued wherein the duration of continuing the current pulse is adjusted not to exceed a limit value of maximal about 600 µs after the loss of physical contact between the electrodes and the implant material is detected.

LIST WITH REFERENCE SIGNS 1 electrode
2 implant (metallic)
3 shunt
4 current source
5 activation switch (e.g. foot switch)
6 safety device
7 lagging element
8 voltage control unit
9 current control unit 10 sensor wires (voltage control)
11 current wires (high current to electrodes)
12 sensor wires (current control)

The invention claimed is:

1. A medical DC-impulse generator of a medical/surgical bipolar fragmentation device, operating on direct electric current, and adapted to fragment a medical implant comprising an electrically conductive material, the medical DC-impulse generator comprising:

an electric current source and an electric current control device with the medical DC-impulse generator being adapted to be connected to a medical endoscopic instrument having a distal end portion and at least two electrodes at said distal end portion that are adapted to physically contact the medical implant, and to apply a direct electric current of predetermined or adjustable strength in a pulsed or timed way to the at least two electrodes, such that the direct electric current flows from one of the at least two electrodes to another of the at least two electrodes via the electrically conductive material of the medical implant and thereby applies electrical energy onto the implant material for cutting said implant material in a cutting process, wherein said electric current control device of the medical DC-impulse generator has a first control portion or an implemented first control process being adapted to apply in a first phase ($t_0$-$t_1$) an electric current after a physical contact between the at least two electrodes of the medical endoscopic instrument and the medical implant is established for melting the implant material, and said electric current control device is adapted to detect a physical contact loss between at least one of the at least two electrodes and the implant material and once the physical contact loss between the at least one of the at least two electrodes and the medical implant is detected, said electric current control device is adapted to start a second control portion or an implemented second control process being adapted to maintain an electric arc between the at least one of the at least two electrodes and the medical implant in a second phase ($t_1$-$t_2$) by allowing an electric current to flow through the implant material for a predetermined maximal maintaining duration, wherein the predetermined maximal maintaining duration is pre-adjusted to a value safely avoiding re-solidification of the implant material by continuing a transfer of the electrical energy into the implant material via the electric arc before a separation / dissection of the medical implant is completed.

2. The medical DC-impulse generator according to claim 1, wherein the electric current control device contains a safety device, which is electrically connected to the electric current source and adapted to limit a maximal duration of a current pulse in the first phase to a maximum first pulse width.

3. The medical DC-impulse generator according to claim 1, wherein the electric current control device contains a lagging element, which is electrically connected to the electric current source and adapted to maintain and limit a maximal duration of the current pulse in the second phase to a maximum second pulse width.

4. The medical DC-impulse generator according to claim 3, wherein the second phase has a duration or pulse width between 50 μs and 600 μs.

5. The medical DC-impulse generator according to claim 3, wherein the lagging element is activated by either a voltage rise at the at least two electrodes to a predetermined value or by a voltage reduction at a shunt which is electrically connected in series with wires connecting the electric current source with the at least two electrodes.

6. The medical DC-impulse generator according to claim 1, wherein a sum of a duration of the first phase and the second phase is shorter than 120 ms.

7. The medical DC-impulse generator according to claim 1, wherein the electric current source is adapted to limit a voltage value at the at least two electrodes in the second phase to a maximum value of approximately 4 V.

8. The medical DC-impulse generator according to claim 1, wherein the at least two electrodes are made from a heat-resistant material, in particular silver, whose resistance-adjusted specific melting energy is larger than $35 \cdot 10^{15}$ J $m^{-4} \Omega^{-1}$.

9. The medical DC-impulse generator according to claim 8, wherein the at least two electrodes are made from a heat-resistant material, in particular silver, whose resistance-adjusted specific melting energy is larger than $100 \cdot 1015$ J m-4 Ω-1.

10. The medical DC-impulse generator according to claim 1, wherein the medical endoscopic instrument is adapted to be inserted into a working channel of a standard endoscope.

11. The medical DC-impulse generator according to claim 1, wherein the medical endoscopic instrument further comprises a distal instrument head on which at least two mutually opposing instrument branches are arranged which define a cutting gap between said at least two mutually opposing instrument branches for receiving the electrically conductive material of the medical implant, wherein mutually facing sides of the at least two mutually opposing instrument branches each form one of the at least two electrodes or are each equipped with one of the at least two electrodes, and the at least two electrodes are shaped to form a punctiform contact area with the implant material at mutually facing electrode sides of the at least two electrodes.

12. A medical DC-impulse generator of a medical/surgical bipolar fragmentation device, operating on direct electric current, and adapted to fragment a medical implant comprising an electrically conductive material, the medical DC-impulse generator comprising:

an electric current source and an electric current control device with the medical DC-impulse generator being adapted to be connected to a medical endoscopic instrument having a distal end portion and at least two electrodes at said distal end portion that are adapted to physically contact the medical implant, and to apply a direct electric current of predetermined or adjustable strength in a pulsed or timed way to the at least two electrodes, such that the direct electric current flows from one of the at least two electrodes to another of the at least two electrodes via the electrically conductive material of the medical implant and thereby applies electrical energy onto the implant material for cutting said implant material in a cutting process, wherein said electric current control device of the medical DC-impulse generator has a first control portion or an implemented first control process being adapted to apply in a first phase ($t_0$-$t_1$) an electric current after a physical contact between the at least two electrodes of the medical endoscopic instrument and the medical implant is established for melting the implant material, and said electric current control device is adapted to detect a physical contact loss between at least one of the at least two electrodes and the implant material and once the physical contact loss between the at least one of the at least two electrodes and the medical implant is detected, said electric current control device is adapted to start a second control portion or an implemented second control process being adapted to maintain an electric arc between the at least one of the at least two electrodes and the medical implant in a second phase ($t_1$-$t_2$) by allowing an electric current to flow through the implant material for a predetermined maximal maintaining duration, wherein the predetermined maximal maintaining duration is pre-adjusted to a value safely avoiding re-solidification of the implant material by continuing a transfer of the electrical energy into the implant material via the electric arc before a separation / dissection of the medical implant is completed, and wherein in the first phase ($t_0$-$t_1$) of direct contact between the at least two electrodes and the medical implant, a current value of the electric current flowing between the at least two electrodes through the implant material is controlled by the electric current control device to generate an electrical energy density at a contact portion between the at least two electrodes and the medical implant adapted to melt the implant material exclusively at the contact portion, the physical contact loss between the at least one of the at least two electrodes and the medical implant being detected by measuring an abrupt decrease of a current value by a current meter and/or an abrupt increase of a voltage value by a volt meter, and in the second phase ($t_1$-$t_2$) of the physical contact loss between the at least one of the at least two electrodes and the medical implant, the voltage value induced by the electric current is controlled by the electric current control device to allow the electric arc to extend between the at least one of the at least two electrodes and the medical implant, wherein the voltage value is limited to a predetermined maximum value below a biocompatible voltage value.

13. The medical DC-impulse generator according to claim 12, wherein the electric energy density introduced into the medical implant by the electric arc is adapted to dissect a metal of the medical implant.

14. The medical DC-impulse generator according to claim 12, wherein the current value is controlled to be greater than 100 amperes.

15. The medical DC-impulse generator according to claim 14, wherein the current value is controlled to be between 140-155 amperes.

16. The medical DC-impulse generator according to claim 12, wherein the voltage value is controlled to be below a limit of approximately 4 volts at the at least two electrodes for a low voltage.

17. The medical DC-impulse generator according to claim 16, wherein the voltage value is controlled to be between 2-4 volts at the at least two electrodes.

18. A bipolar fragmentation device operating on direct electric current and being adapted to fragment a medical implant comprising an electrically conductive material such as metal, the bipolar fragmentation device comprising:
a medical endoscopic instrument having a distal end and at least two electrodes at said distal end; and
a medical DC-impulse generator, the medical DC-impulse generator comprising an electric current source and an electric current control device with the medical DC-impulse generator being adapted to be connected to the bipolar fragmentation device, the at least two electrodes being adapted to physically contact the medical implant, and to apply a direct electric current of predetermined or adjustable strength in a pulsed or timed way to the at least two electrodes, such that the electric current flows from one of the at least two electrodes to another of the at least two electrodes via the electrically conductive material of the medical implant and thereby applying electrical energy onto the implant material for cutting said implant material in a cutting process,
wherein said electric current control device of the medical DC-impulse generator has a first control portion or an implemented first control process being adapted to apply in a first phase ($t_0$-$t_1$) an electric current after a physical contact between the at least two electrodes and the medical implant for melting the implant material is established, and
said electric current control device is adapted to detect a physical contact loss between at least one of the at least two electrodes and the implant material and once the physical contact loss between the at least one of the at least two electrodes and the medical implant is detected, said electric current control device is adapted to start a second control portion or an implemented second control process being adapted to maintain an electric arc between the at least one of the at least two electrodes and the medical implant in a second phase ($t_1$-$t_2$) by allowing an electric current to flow through the implant material for a predetermined maximal maintaining duration,
wherein the predetermined maximal maintaining duration is pre-adjusted to a value safely avoiding re-solidification of the implant material by continuing a the transfer of the electrical energy into the implant material via the electric arc before a separation/ dissection of the medical implant is completed.

19. A medical DC-impulse generator of a medical/surgical bipolar fragmentation device, operating on direct electric current, and adapted to fragment a medical implant comprising an electrically conductive material and located within a patient's body, the medical DC-impulse generator comprising:
an electric current source and an electric current control device with the medical DC-impulse generator being adapted to be connected to a medical endoscopic instrument having a distal end portion and at least two electrodes at said distal end portion that are adapted to physically contact the medical implant, and to apply a direct electric current of predetermined or adjustable strength in a pulsed or timed way to the at least two electrodes, such that the electric current flows from one of the at least two electrodes to another of the at least two electrodes via the electrically conductive material of the medical implant and thereby applies electrical energy onto the implant material for cutting said implant material in a cutting process,
wherein said electric current control device of the medical DC-impulse generator has a first control portion or an implemented first control process being adapted to apply in a first phase (t0-t1) an electric current after a physical contact between the at least two electrodes of the medical endoscopic instrument and the medical implant is established for melting the implant material, and
said electric current control device is adapted to detect a physical contact loss between at least one of the at least two electrodes and the medical implant and once the physical contact loss between the at least one of the at least two electrodes and the implant material is detected, said electric current control device is adapted to start a second control portion or an implemented second control process being adapted to maintain an electric arc between the at least one of the at least two electrodes and the medical implant in a second phase (t1-t2) by allowing an electric current to flow through the implant material for a predetermined maximal maintaining duration, wherein the predetermined maximal maintaining duration is pre-adjusted to a value safely avoiding re-solidification of the implant material by continuing a transfer of the electrical energy into the implant via the electric arc before a separation/dissection of the medical implant is completed, and wherein in the first phase (t0-t1) of direct contact between the at least two electrodes and the medical implant, a current value of the electric current flowing between the at least two electrodes through the implant material is controlled by the electric current control device to generate an electrical energy density at a contact portion between the at least two electrodes and the medical implant adapted to melt the implant material exclusively at the contact portion, the physical contact loss between the at least one of the at least two electrodes and the medical implant being detected by measuring an abrupt decrease of a current value by a current meter and/or an abrupt increase of a voltage value by a volt meter, and in the second phase (t1-t2) of the physical contact loss between the at least one of the at least two electrodes and the medical implant, the voltage value induced by the electric current is controlled by the electric current control device to allow the electric arc to extend between at least one of the at least two electrodes and the medical implant, wherein the voltage value is limited to a predetermined maximum value below a biocompatible voltage value, and wherein the predetermined maximal maintaining duration is defined to avoid unintended effects on the patient's body through a faradic effect and/or an electrolytic effect.

* * * * *